United States Patent [19]
Arcara

[11] Patent Number: 4,527,418
[45] Date of Patent: Jul. 9, 1985

[54] METHOD OF MEASURING SPECIFIC GRAVITY AND APPARATUS UTILIZING THE SAME

[75] Inventor: Samuel A. Arcara, Doylestown, Pa.
[73] Assignee: Honeywell Inc., Minneapolis, Minn.
[21] Appl. No.: 578,736
[22] Filed: Feb. 9, 1984
[51] Int. Cl.$^3$ .............................................. G01N 9/32
[52] U.S. Cl. ........................................ 73/30; 73/32 R
[58] Field of Search ..................... 73/30, 23, 55, 32 R; 364/509, 558; 137/91

[56] References Cited

U.S. PATENT DOCUMENTS 3,878,376 4/1975 Sholes, Jr. et al. ................. 364/558
4,285,245 8/1981 Kennedy ............................. 73/199

Primary Examiner—Stephen A. Kreitman
Attorney, Agent, or Firm—Mitchell J. Halista; Trevor B. Joike

[57] ABSTRACT

A method of measuring the specific gravity of a fluid to be analyzed includes the steps of pressurizing a fixed volume chamber by the fluid to be analyzed, allowing the pressure in the chamber to decay through a fixed restriction between predetermined pressure limits, measuring the time interval of the pressure decay between the pressure limits and converting the time interval value to the specific gravity of the fluid to be analyzed. The apparatus utilizing the aforesaid method includes a fixed volume chamber, first valve means for admitting a pressurized fluid to be analyzed into the chamber to pressurize the chamber to a first pressure level, second valve means for exhausting the pressurized fluid from the chamber through the fixed restriction, pressure sensing means for monitoring the pressure decay in the chamber during the exhaust of the pressurized fluid, time interval measuring means for producing a time interval value representative of the time required by the pressure decay between predetermined pressure limits lower than the first pressure level and computing means for converting the time interval value to the specific gravity of the fluid to be analyzed.

12 Claims, 1 Drawing Figure

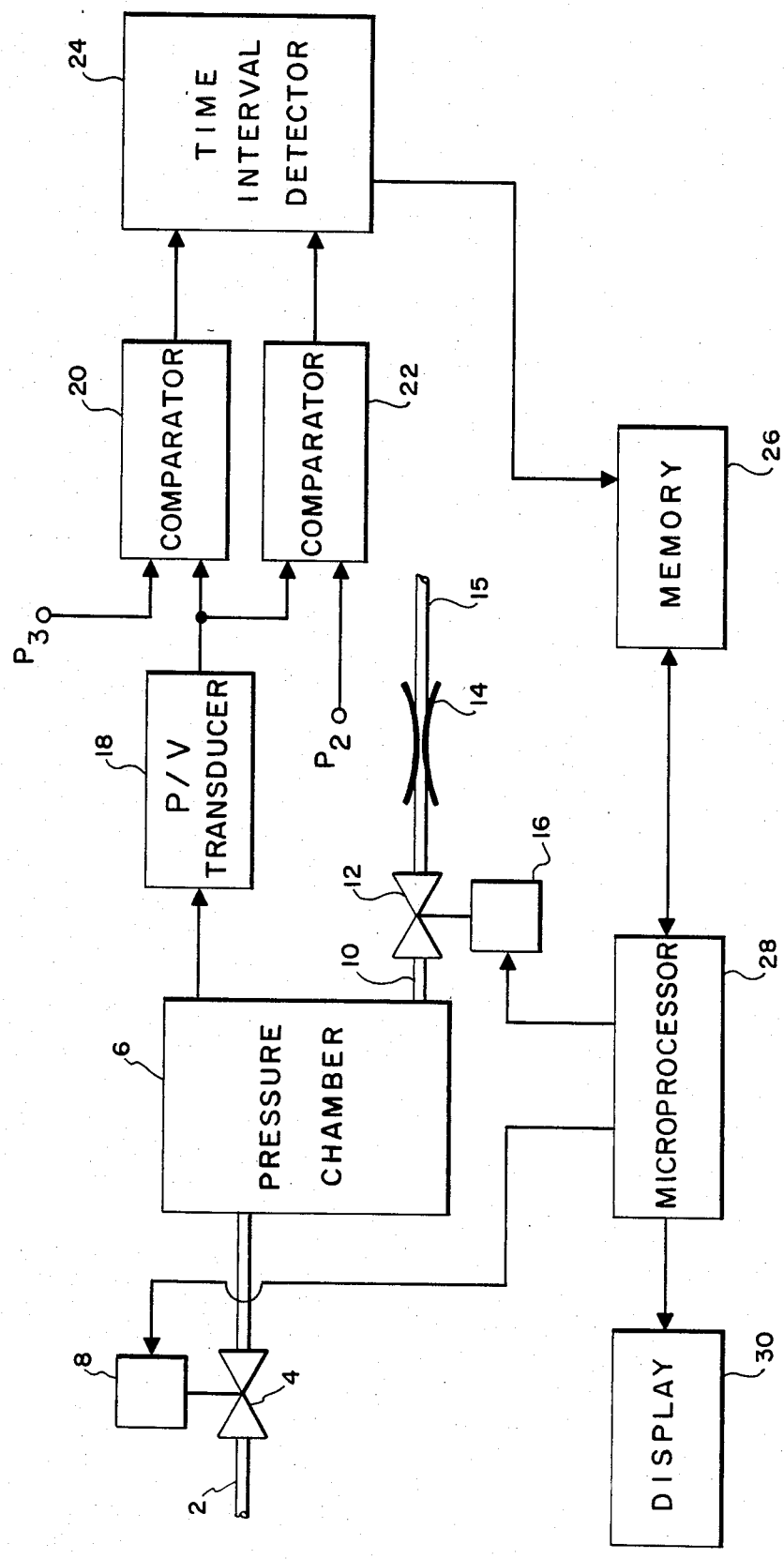

METHOD OF MEASURING SPECIFIC GRAVITY AND APPARATUS UTILIZING THE SAME

BACKGROUND OF THE INVENTION

1. Field of the Invention

The present invention is directed to a method and apparatus for measuring specific gravity. More specifically, the present invention is directed to a method and apparatus for measuring the specific gravity of a pressurized fluid.

SUMMARY OF THE INVENTION

The present invention relates to an improved method and apparatus for measuring specific gravity of a pressurized fluid.

In accomplishing this and other objects, there has been provided, in accordance with the present invention, as method and apparatus for measuring the specific gravity of a pressurized fluid including the steps of pressurizing a fixed volume chamber by the fluid to be analyzed, allowing the pressure in the chamber to decay through a fixed restriction between predetermined pressure limits, measuring the time interval of the pressure decay between the pressure limits and converting the time interval value to the specific gravity of the fluid to be analyzed. The apparatus utilizing the aforesaid method includes a fixed volume chamber, first means for admitting a pressurized fluid to be analyzed into the chamber to pressurize the chamber to a first pressure level, second valve means for exhausting the pressurized fluid from the chamber through the fixed restriction, pressure sensing means for monitoring the pressure decay in the chamber during the exhaust of the pressurized fluid, time interval measuring means for producing a time interval value representative of the time required by the pressure decay between predetermined second and third pressure limits lower than the first pressure level and computing means for converting the time interval value to the specific gravity of the fluid to be analyzed.

BRIEF DESCRIPTION OF THE DRAWING

A better understanding of the present invention may be had when the following detailed description is read in connection with the accompanying drawing, in which the single FIGURE is a block diagram of a specific gravity measuring apparatus utilizing the method of the present invention.

DESCRIPTION OF THE PREFERRED EMBODIMENT

Detailed Description

Referring to the single FIGURE drawing in more detail, there is shown an apparatus for measuring the specific gravity of a pressurized fluid using the method of the present invention. An input pipeline 2 is arranged to be connected to the source of the fluid to be analyzed. The input pipeline 2 is connected through a valve 4 to a fixed volume pressure chamber 6. The valve 4 may advantageously be a solenoid operated valve having an operating solenoid 8. The pressure chamber 6 is connected to an exhaust line 10 which is connected through a second valve 12 to a fixed line restriction 14. The line restriction 14 is arranged to have an outlet 15 for exhausting the fluid to be analyzed. The second valve 12 may advantageously also be in a form of a solenoid operated valve having an operating solenoid 16.

A pressure-to-voltage transducer 18 is connected to the pressure chamber 6 to produce an output signal representative of the output pressure from the pressure chamber 6. The output signal of the transducer 18 is connected to a first input of a first comparator 20 and a first input of a second comparator 22. A second input of the first comparator 22 is connected to a source of a signal representing a second pressure level $P_2$ while the second input of the second comparator 20 is connected to a signal source representing a third pressure level $P_3$. The outputs of the first and second comparators 20, 22 are connected to a time interval detector 24 for determining the time interval between the output signals from the first and second comparators 20, 22. The output of the time interval detector 24 is connected to a memory 26 for storing the time interval measurements from the time interval detector 24. The data representing the time interval measurement stored in the memory 26 is arranged to be read by a microprocessor 28 for calculating the specific gravity of the fluid to be measured, as described more fully hereinafter. A display 30 which may include a printer is connected to the microprocessor 28 for recording and/or displaying the specific gravity of the fluid to be analyzed.

MODE OF OPERATION

The apparatus shown in the single FIGURE drawing operates by pressurizing the pressure chamber 6 by the pressurized gas to be analyzed to a first pressure level $P_1$ greater than the second pressure level $P_2$ through the control valve 4. After the pressure chamber 6 is pressurized, the control valve 4 is closed, and the control valve 12 is opened to allow the pressure in the pressure chamber 6 to decay by exhausting the stored fluid through the restriction 14. The pressure in the pressure chamber 6 is monitored by the transducer 18 which produces an electrical output signal indicative of the pressure within the pressure chamber 6. This output signal is applied to the first and second signal comparators 20, 22 to produce an output signal from the first comparator 20 when the pressure in the pressure chamber 6 reaches the second pressure level $P_2$ and an output from the second comparator 22 when the pressure in the pressure chamber 6 reaches a third pressure level $P_3$. The time between the pressure levels $P_2$ and $P_3$ is detected by the time interval detector 24 and converted to a time interval value in a digital form, e.g., a count stored in a counter counting signals from a fixed frequency oscillator.

The digital output from the detector 24 is stored in the memory 26 which is preferably a random access memory (RAM) used to concurrently store an operating program for the microprocessor 28, which program is used, stored, read and utilized in a well-known fashion to effect a logic operation of the microprocessor 28 to calculate the specific gravity to the fluid to be analyzed and to provide the aforesaid sequentially operation of the first and second valves 8, 12. Initially, a reference fluid is supplied to the illustrated apparatus through input line 2 and its decay time ($t_1$) is detected and stored in the memory 26. Additionally, a digital representation of the specific gravity ($SG_1$) of the reference fluid is also stored in the memory 26. Subsequently, the illustrated apparatus is connected to a source of the fluid to be analyzed and the decay time ($t_2$) of the fluid to be analyzed is detected and stored in the memory 26 to be used in calculating the specific gravity ($SG_2$) of the fluid to be analyzed.

The pressure in the chamber 6 decays exponentially through the restriction 14 between $P_2$ and $P_3$ as follows:

$$P_3 = P_2 e^{-t/\tau}$$

Where t equals the time interval for the pressure to decay from $P_2$ to $P_3$ $$\tau = \frac{V_o \sqrt{SG}}{K}$$

where
K = orifice flow constant
$V_o$ = volume of chamber 6
SG = specific gravity of the fluidpe Assuming that $V_o/K$ is a constant for two fluids of specific gravity $SG_1$ and $SG_2$:

$$P_3 = P_2 e^{-t_1/\tau_1} = P_2 e^{-t_2/\tau_2}$$

Where $t_1$ = time interval of decay for a fluid of specific gravity $SG_1$; $t_2$ = time interval for decay of a fluid of specific gravity $SG_2$;

Solving for $SG_2$:

$$\frac{t_1}{\tau_1} = \frac{t_2}{\tau_2}$$

$$\tau_2 = \frac{t_2}{t_1} \tau_1$$

$$\text{THUS } \frac{V_o \sqrt{SG_2}}{K} = \frac{t_2}{t_1} \frac{V_o \sqrt{SG_1}}{K} \text{ AND}$$

$$SG_2 = \left(\frac{t_2}{t_1}\right)^2 SG_1$$

Therefore, by measuring the decay time ($t_1$) of a reference fluid of known specific gravity $SG_1$, the specific gravity $SG_2$ of another fluid can be computed from its decay time ($t_2$) using the above final equation.

Accordingly, it may be seen, that there has been provided, in accordance with the present invention an improved method and apparatus for measuring a specific gravity of a pressurized fluid.

What is claimed:

1. A method for measuring the specific gravity of a pressurized fluid including the steps of
   pressurizing a fixed volume chamber by the fluid to be analyzed to a first pressure level,
   allowing the pressure in the chamber to decay through a fixed restriction,
   measuring the decay time of the pressure between preset second and third pressure limits lower than the first pressure level and
   converting the decay time into the specific gravity of the fluid to be analyzed.

2. A method as set forth in claim 1 and including the further step of providing the decay time in a digital representation thereof prior to converting the decay time into the specific gravity of the fluid to be analyzed.

3. A method as set forth in claim 2 wherein the converting of the decay time includes the step of displaying the specific gravity of the fluid to be analyzed.

4. A method as set forth in claim 1 wherein the step of converting includes the step of comparison of the decay time of the fluid to be analyzed with the decay time of a reference fluid having a known specific gravity.

5. A method as set forth in claim 4 wherein the step of comparison includes the step of computing the specific gravity $SG_2$ of the fluid to be analyzed according to the relationship $$SG_2 = \left(\frac{t_2}{t_1}\right)^2 SG_1$$

where $SG_1$ is the specific gravity of the reference fluid, $t_1$ is the decay time of the reference fluid and $t_2$ is the decay time of the fluid to be analyzed.

6. A specific gravity measuring apparatus comprising
   a fixed volume chamber,
   first means for pressurizing said chamber to a first pressure level by a fluid to be analyzed,
   a fixed restriction, a second means for allowing a pressure in said chamber to decay through said fixed restriction,
   pressure sensing means for monitoring the pressure decay in said chamber,
   time interval means for producing a time interval value representative of the time required by the pressure decay between predetermined second and third pressure limits lower than the first pressure level and
   computing means for converting the time interval value to the specific gravity of the fluid to be analyzed.

7. A measuring apparatus as set forth in claim 6 wherein said first means includes a first valve means for admitting the fluid to be analyzed into said chamber.

8. A measuring apparatus as set forth in claim 7 wherein said second means includes a second valve means connected between said chamber and said restriction.

9. A measuring apparatus as set forth in claim 6 wherein said time interval means includes a first signal comparator means for comparing an output from said sensing means with a signal representative of the second pressure limit and a second signal comparator for comparing the output from said sensing means with a signal representative of the third pressure limit, said first and second comparators producing respective output signals upon the detection of an equality between their compared input signals.

10. A measuring apparatus as set forth in claim 9 wherein said time interval means includes means for converting a time interval between the occurrence of the output signals from said first and second comparators into a digital representation thereof and said computing means includes a digital computer means for utilizing said digital representation in the converting of the time interval into the specific gravity of the fluid to be analyzed.

11. A measuring apparatus as set forth in claim 10 wherein said computing means is arranged to compute the specific gravity $SG_2$ of a fluid to be analyzed according to the relationship $$SG_2 = \left(\frac{t_2}{t_1}\right)^2 SG_1$$

where $t_1$ is the decay time of a reference fluid, $t_2$ is the decay time of the fluid to be analyzed and $SG_1$ is the specific gravity of the reference fluid.

12. A measuring apparatus as set forth in claim 11 wherein said computing means includes a display means for displaying the specific gravity of the fluid to be analyzed.

* * * * *